United States Patent
Martin et al.

(10) Patent No.: US 8,663,323 B2
(45) Date of Patent: Mar. 4, 2014

(54) ITEM COMPOSED OF A SILICON GEL CONTAINING AN ODOR MASKING ACTIVE INGREDIENT

(75) Inventors: François Martin, Luebeck (DE); Mathias Appelt, Luebeck (DE)

(73) Assignees: Bluestar Silicones France SAS, Lyons (FR); Bluestar Silicones Germany, Lubeck (DE)

( * ) Notice: Subject to any disclaimer, the term of this patent is extended or adjusted under 35 U.S.C. 154(b) by 319 days.

(21) Appl. No.: 12/531,379

(22) PCT Filed: Mar. 14, 2008

(86) PCT No.: PCT/FR2008/000333
§ 371 (c)(1),
(2), (4) Date: May 28, 2010

(87) PCT Pub. No.: WO2008/129171
PCT Pub. Date: Oct. 30, 2008

(65) Prior Publication Data
US 2010/0241226 A1 Sep. 23, 2010

(30) Foreign Application Priority Data

Mar. 15, 2007 (FR) .................................. 07 53858

(51) Int. Cl.
*A61F 2/16* (2006.01)
*A61F 2/52* (2006.01)

(52) U.S. Cl.
USPC ............................................................ 623/7

(58) Field of Classification Search
USPC .................................. 623/7–8; 450/30–93
See application file for complete search history.

(56) References Cited

U.S. PATENT DOCUMENTS

| | | | |
|---|---|---|---|
| 5,466,726 A | 11/1995 | Inoue et al. | |
| 5,534,609 A | 7/1996 | Lewis et al. | |
| 5,990,377 A * | 11/1999 | Chen et al. | 604/381 |
| 6,083,602 A * | 7/2000 | Caldwell et al. | 428/77 |
| 6,162,250 A | 12/2000 | Malice, Jr. et al. | |
| 6,171,647 B1 * | 1/2001 | Holman | 427/202 |
| 6,203,810 B1 * | 3/2001 | Alemany et al. | 424/404 |
| 6,235,861 B1 | 5/2001 | Kishi | |
| 6,420,037 B1 | 7/2002 | Tsuji et al. | |
| 6,649,805 B1 * | 11/2003 | Carlucci et al. | 604/359 |
| 6,972,313 B2 | 12/2005 | Howe et al. | |
| 7,988,986 B2 * | 8/2011 | Beisang et al. | 424/422 |
| 2003/0023216 A1 * | 1/2003 | Carlucci et al. | 604/375 |
| 2003/0163197 A1 * | 8/2003 | Chen | 623/7 |
| 2003/0220048 A1 * | 11/2003 | Toro et al. | 450/57 |
| 2005/0118383 A1 * | 6/2005 | Cargill et al. | 428/68 |
| 2005/0208100 A1 * | 9/2005 | Weber et al. | 424/426 |
| 2007/0055371 A1 * | 3/2007 | Laghi | 623/7 |
| 2007/0259017 A1 * | 11/2007 | Francis | 424/423 |
| 2008/0160064 A1 * | 7/2008 | Capelli et al. | 424/423 |
| 2008/0234645 A1 * | 9/2008 | Dodge et al. | 604/368 |
| 2008/0242794 A1 * | 10/2008 | Sandford et al. | 524/515 |
| 2009/0123525 A1 * | 5/2009 | Bedard | 424/443 |
| 2009/0214652 A1 * | 8/2009 | Hunter et al. | 424/486 |
| 2010/0023123 A1 * | 1/2010 | Laghi | 623/7 |
| 2010/0215708 A1 * | 8/2010 | Zumbuehl et al. | 424/422 |
| 2011/0171880 A1 * | 7/2011 | Nam | 450/81 |
| 2012/0045636 A1 * | 2/2012 | Obae et al. | 428/221 |
| 2012/0135060 A1 * | 5/2012 | Bukshpan et al. | 424/404 |

FOREIGN PATENT DOCUMENTS

FR 2770220 A1 4/1999

* cited by examiner

*Primary Examiner* — Suzette J Gherbi
(74) *Attorney, Agent, or Firm* — Dentons US LLP

(57) ABSTRACT

The present invention relates to an item, such as an external breast prosthesis, an anti-decubitus cushion or mattress, comprising a closed envelope A made of a soft material and containing as filler a silicone gel that comprises an odor masking active ingredient C.

10 Claims, No Drawings

ITEM COMPOSED OF A SILICON GEL CONTAINING AN ODOR MASKING ACTIVE INGREDIENT

CROSS-REFERENCE TO PRIORITY APPLICATIONS

This application claims priority under 35 U.S.C. §119 of FR 0753858, filed Mar. 15, 2007, and is a continuation/national phase of PCT/FR 2008/000333, filed Mar. 14, 2008, and designating the United States (published in the French language on Oct. 30, 2008, as WO 2008/129171 A1; the title and abstract were also published in English), each hereby expressly incorporated by reference in its entirety and each assigned to the assignee hereof.

The present invention relates to an article, such as an external mammary prosthesis, an anti-eschar cushion or an anti-eschar mattress, comprising a closed envelope A formed from a supple material B containing as filling material a silicone gel comprising an antiodor active principle C.

Silicone gels and other gels are commonly used in the medical field, whether for external use (mammary prostheses, or medical cushions or mattresses) or for internal use (implanted mammary prostheses). They are of great mobility and have very good mechanical properties, their density being close to that of human tissue.

Specifically, there are a relatively large number of types of external mammary prosthesis intended to be placed in a bra cup. The first mammary prostheses were made of low-density molded polyurethane. Like inflatable plastic mammary prostheses that were developed later, they had the drawback of not having the same mobility as a real breast, of being lighter, which created an imbalance in the wearer, and of not staying in place very well.

Molded silicone mammary prostheses that have the shape of a breast are known. However, their weight does not correspond exactly, and they do not have the same natural movements.

At the present time, many models of external mammary prosthesis contain a supple envelope formed from a polyurethane film, filled with a silicone gel.

Another field in which silicone gels are frequently used is that of the prevention of pressure sores.

It is known that people who are obliged to remain for a long time in a seated or laying position are exposed to the risk of formation of pressure sores resulting from prolonged tissue compression that prevents the blood from circulating, which leads to necrosis and then to decomposition of the tissues, which become infected.

Pressure sores are a major problem for people of reduced mobility (wheelchair users, the elderly, the bedridden, etc.) or for whom certain tissue surfaces are lacking in sensation. Pressure sores are ulcers (cutaneous and subcutaneous ischaemic necrosis) arising following the prolonged and continual pressing of a bony relief on a hard surface. Also known as wounds, ulcers or eschars, they generally appear in regions of the body having a bony protruberance close to the skin. Medical cushions or mattresses are still at the present time the most effective method of prevention.

Anti-eschar cushions and mattresses formed from inflatable bags or from bags filled with a liquid or gel, or alternatively cushions or mattresses made of a cellular material, are already known.

However, when silicone gels are used as filling material for bags or envelopes made of supple material, in particular for envelopes of the polyurethane-based plastic film type or of the silicone elastomer type, for the preparation of an article such as an external mammary prosthesis or a medical cushion or mattress, they have the drawback of giving off an unpleasant odor when the silicone gel is vulcanized during the preparation and forming of the article by molding or any other technique known to those skilled in the art. Specifically, to make these articles, a silicone composition that is a precursor of a silicone gel is placed in a bag or envelope made of supple material and the filling material is polymerized in a mold by raising the temperature or vulcanization. The interaction between the silicone gel and the envelope, in particular when it is of the polyurethane film type, combined with raising of the temperature during the vulcanization appears to generate degradation products that are responsible for the appearance of nauseating odors.

In this state of knowledge, one of the essential objectives of the present invention is to provide an article comprising a closed envelope formed from a supple material of the polyurethane-based plastic film type or of the silicone elastomer type and containing a silicone gel as filling material, and which does not have the odor problems mentioned above.

The Applicant has mobilized substantial research means and conducted numerous experiments to achieve this objective, among others, as a result of which it has, to its credit, entirely surprisingly and unexpectedly, found that it is beneficial to introduce into a standard silicone composition, capable of crosslinking to form a silicone gel, an aluminosilicate in order to eliminate the odor problems in the abovementioned applications.

One subject of the present invention is an article comprising a closed envelope A formed from a supple material, preferably of the polyurethane-based plastic film type or of the silicone elastomer type, said closed envelope A containing as filling material a silicone gel obtained by crosslinking a silicone composition B that can be crosslinked into a gel by hydrosilylation, characterized in that said silicone composition B comprises at least one antiodor active principle C chosen from the group formed by an aluminosilicate, a cyclodextrin and a compound having an open or closed cage structure.

According to the essential characteristics of the invention, the article comprising a closed envelope A formed from a supple material preferably of the polyurethane-based plastic film type or of the silicone elastomer type in question is characterized essentially in that it contains as filling material a silicone gel comprising an antiodor active principle C chosen from the group formed by an aluminosilicate, a cyclodextrin and a compound having an open or closed cage structure.

According to one advantageous embodiment, the antiodor active principle C is an aluminosilicate, preferably a zeolite and even more preferentially a synthetic zeolite.

Zeolites are crystalline porous materials. Structurally, a zeolite is an assembly of crystalline aluminosilicate cages. The unit cage consists of an assembly of tetrahedra associating aluminum oxide and silicon oxide complexes, and sharing the oxygen atoms. A zeolite is thus characterized by an assembly of tetrahedra $QO_4$, in which Q represents in general the Si and Al atoms, but also Ti, Ge, B, Fe and Ga. The anionic charges are equilibrated by the presence of alkali metal or alkaline-earth metal cations (Na, K, Li, Ca) and is finally organized according to the formula $M_{x/n}[Al_xSi_yO_{2(x+y)}] \cdot zH_2O$. Depending on the value of the ratio y/x, the structures may be classified into several types. More than 120 types of elemental structure have been found, classified according to a three-letter code by the International Zeolite Association. A definition of these codes is described, for example, in the zeolite structure review: Ch. Baerlocher, W. W. Meier, D. H.

Oison, *Atlas of zeolite framework types*, fifth revised edition, Elsevier, Amsterdam 2001, 3-18.

Zeolite syntheses are described, for example, in the publications H. Kessler, *Synthesis of Molecular Sieves, Comprehensive Supramolecular Chemistry*, G. Alberti, T. Bein (Eds.), Vol. 7 Pergamon, Oxford, 1996, 425-464 and C. S. Cundy and P. A. Cox, *The Hydrothermal Synthesis of Zeolites: History and Development from the Earliest Days to the Present Time*, Chem. Rev. 2003, 103, 663-701.

A compound with an open or closed cage structure is a compound comprising at least 4 atoms of an element chosen from the elements from columns 3 to 13 of the Periodic Table, and at least 4 oxygen atoms, said atoms of said element being bonded only to oxygen atoms and to one or more identical or different substituents.

For the purposes of the present invention, the term "compound with a cage structure" means a compound in which the arrangement of the atoms of said element and of the oxygen atoms, and the arrangement of the bonds between the atoms of said element and of the oxygen atoms form at least three faces and preferably four faces of at least one polyhedron, the apices of the faces being formed by said atoms, and the edges of the faces being formed by said bonds.

For the purposes of the present invention, the term "closed cage" means a cage in which all the edges of said polyhedron (polyhedra) constitute a bond between an atom of said element and an oxygen atom.

For the purposes of the present invention, the term "open cage" means a cage in which certain edges of said polyhedron (polyhedra) do not constitute a bond between an atom of said element and an oxygen atom.

Preferably, said compound(s) comprise(s) between 4 and 20, preferably between 4 and 12 and better still 6, 7, 8, 9, 10 or 12 atoms of said element from columns 3 to 13.

Silicone gels are conventionally obtained by crosslinking a silicone composition comprising:
- at least one polyorganosiloxane (A) containing on average two alkenyl groups bonded to silicon per molecule, said alkenyl groups each containing 2 to 6 carbon atoms, and no silicon atom being bonded to more than one alkenyl group,
- at least one hydrogen-bearing silicone compound (B) containing at least two and preferably at least three hydrogen atoms bonded to silicon per molecule,
- optionally, at least one nonfunctionalized polyorganosiloxane (C), and
- a platinum-based hydrosilylation catalyst (D).

For all these applications, the physical properties of these gels are adapted according to the use by varying the contents of siloxyl units bearing vinyl and SiH functions.

In general, the polydiorganosiloxane (A) contains on average two alkenyl groups bonded to silicon per molecule, each alkenyl group being bonded to a different silicon atom. The polydiorganosiloxane (A) is a substantially linear polymer, although a small degree of branching may exist. Preferably, the alkenyl groups are attached to silicon atoms that are distant from each other in the molecule, and, at best, they are attached to the terminal silicon atoms of the siloxane chain. The alkenyl groups contain at most 6 carbon atoms and they may be, for example, vinyl, allylic or hexenyl groups, although they are preferably vinyl groups. The remaining organic substituents on the polydiorganosiloxane (A) are chosen from alkyl and aryl groups, and are preferably alkyl groups containing not more than 8 carbon atoms, and phenyl groups. Examples of these remaining substituents are methyl, ethyl, propyl, isobutyl and phenyl groups. The compounds most readily used are $\alpha,\omega$-(dimethylvinylsiloxy) polydimethylsiloxanes or polyorganosiloxanes of poly(dimethylsiloxane) (methylvinylsiloxane) $\alpha,\omega$-(dimethylvinylsiloxy) type.

The polydiorganosiloxane (A) is a commercial product, for instance the products of the Rhodorsil® 621V range from the company Bluestar Silicones, and are widely disclosed in the technical literature as regards both their structures and their syntheses.

Preferably, the polydiorganosiloxane (A) is substantially linear and has a dynamic viscosity of less than or equal to 200 000 mPa·s, preferably 170 000 mPa·s and even more preferentially between 20 and 165 000 mPa·s.

According to another variant, the weight percentage of alkenyl reactive groups directly bonded to a silicon atom is between 0.025% and 3%.

The hydrogenated silicon compound (B) is in general a polyorganosiloxane, or a silane, comprising at least 2 and preferably 3 hydrogen atoms bonded to silicon per molecule. These hydrogen atoms may be located on terminal siloxane units and also on siloxane units that are in the polymer chain, or alternatively they may be located only within the siloxane chain.

In practice, the polyorganohydrogenosiloxanes (B) used are, for example, polyorganosiloxanes of poly(dimethyl-siloxy)-(siloxymethylhydrogeno)-$\alpha,\omega$-(dimethylhydrogenosiloxy) type and $\alpha,\omega$-(dimethylhydrogenosiloxy) polydimethylsiloxanes. These POSs (I) are commercial products and are widely disclosed in the technical literature as regards their structures and their syntheses.

For the nonfunctionalized polyorganosiloxanes (C), the ones most readily used are $\alpha,\omega$-(trimethylsiloxy) polydimethylsiloxanes or PDMS. These polyorganosiloxanes are commercial products, for instance the products of the Rhodorsil® 47V range (for example 47V50, 47V100, 47V500, 47V500, 47V12500 or 47V30000) from the company Bluestar Silicones, and are widely disclosed in the technical literature as regards their structures and their syntheses.

Preferably, the nonfunctionalized polyorganosiloxane (C) is substantially linear and has a dynamic viscosity of less than or equal to 50 000 mPa·s and preferably between 20 and 40 000 mPa·s.

The catalyst (D) is another important component of the composition according to the invention. It is preferably an organometallic platinum complex or alternatively one of the platinum-based catalysts conventionally used for the catalysis of hydrosilylation reactions between, for example, groups SiH and groups Si-vinyl. Examples that may be mentioned include platinum black, chloroplatinic acid, a chloroplatinic acid modified with an alcohol, a complex of chloroplatinic acid with an olefin, an aldehyde, a vinylsiloxane or an acetylenic alcohol, inter alia. U.S. Pat. No. 2,823,218 discloses a hydrosilylation catalyst of the chloroplatinic acid type and U.S. Pat. No. 3,419,593 relates to catalysts formed by complexes of chloroplatinic acid and of an organosilicone of the vinylsiloxane type. Complexes of platinum and of hydrocarbons that are useful as hydrosilylation catalysts are disclosed in U.S. Pat. Nos. 3,159,601 and 3,159,662. U.S. Pat. No. 3,723,497 describes a platinum acetylacetonate and U.S. Pat. No. 3,220,972 relates to platinum alkoxide-based catalysts.

For component (D), the term "effective amount of at least one hydrosilylation reaction catalyst" means the amount that is sufficient to initiate the hydrosilylation reaction. As regards the catalytically effective amount to be used, it goes without saying that a person skilled in the art in the field under consideration is entirely capable of determining the optimum amount of catalyst to promote the hydrosilylation reaction.

This amount depends especially on the nature of the catalyst and of the POSs under consideration. To give an idea, it may be indicated that it will be between 0.001% and 0.5% by weight relative to the total weight of the composition.

Preferably, the amount of the constituents (A), (B), (C) and (D) is chosen such that the mole ratio r of the hydrogen atoms bonded to silicon to the alkenyl radicals (X) bonded to silicon is between 0.5:1 and 5:1.

The silicone composition according to the invention may also comprise at least one addition-reaction retardant or a crosslinking inhibitor chosen from the following compounds:

- polyorganosiloxanes substituted with at least one alkenyl that may optionally be in cyclic form, tetramethylvinyltetrasiloxane being particularly preferred,
- pyridine,
- organic phosphines and phosphites,
- unsaturated amides,
- alkyl maleates, and
- acetylenic alcohols.

These acetylenic alcohols (see FR-A-1 528 464 and FR-A-2 372 874), which are among the preferred thermal blockers of the hydrosilylation reaction, have the formula:

$$R'—(R'')C(OH)—C\equiv CH$$

in which formula

R' is a linear or branched alkyl radical, or a phenyl radical;
R'' is H or a linear or branched alkyl radical, or a phenyl radical; the radicals R', R'' and the carbon atom alpha to the triple bond possibly forming a ring; and
the total number of carbon atoms contained in R' and R'' being at least 5 and preferably from 9 to 20.

Said alcohols are preferably chosen from those with a boiling point of greater than 250° C. Examples that may be mentioned include:
1-ethynyl-1-cyclohexanol;
3-methyl-1-dodecyn-3-ol;
3,7,11-trimethyl-1-dodecyn-3-ol;
1,1-diphenyl-2-propyn-1-ol;
3-ethyl-6-ethyl-1-nonyn-3-ol;
2-methyl-3-butyn-2-ol;
3-methyl-1-pentadecyn-3-ol.

These α-acetylenic alcohols are commercial products. Such a retardant is present in a maximum proportion of 3000 ppm and preferably in a proportion of 100 to 1000 ppm relative to the total weight of the polyorganosiloxanes in the silicone composition.

In a manner known per se, the silicone elastomer composition may also be supplemented with various conventional additives, for instance fillers or colorants.

To improve the stability on storage of the composition according to the invention and to provide users with an easily manipulable commercial form, a system is envisioned containing at least two components A and B comprising the constituents (A), (B) and (C) and optionally the constituent (E) of the silicone composition that can be crosslinked into an adhesive gel by hydrosilylation as defined according to the invention, with the condition that the hydrosilylation reaction catalyst (D) is separate from the constituent (B).

To simplify the use, it is preferable to propose a two-component system in which the proportions A:B are between 10:100 and 100:10 and preferably between 40:60 and 60:40, and even more preferentially 50:50 parts by weight approximately.

As regards the preparation of the gel, it may be pointed out that the crosslinking of the composition into a gel takes place at room temperature or after heating to temperatures between 50 and 200° C., for example. In this context, the necessary crosslinking times are, for example, between a few minutes and 1 hour 30 minutes. The crosslinked adhesive gel obtained from the composition described above forms a fully-fledged subject of the present invention.

According to one preferred embodiment, the silicone composition B that can be crosslinked into a gel by hydrosilylation comprises up to 1%, preferably up to 0.5% and even more preferentially between 0.01% and 0.1% by weight, relative to the total weight of said silicone composition B, of said antiodor active principle C.

According to one preferred embodiment of the invention, the article according to the invention is an external mammary prosthesis, an anti-eschar cushion or an anti-eschar mattress.

These products are widely commercially circulated and described and are well known to those skilled in the art.

The invention also relates to:

- the use of at least one aluminosilicate as antiodor active principle C in silicone gels intended for plastic reconstitution prostheses or cushions for orthopaedic use and the like,
- the use of at least one aluminosilicate, a zeolite being particularly preferred and a synthetic zeolite even more preferred, as antiodor active principle C in silicone gels intended for external mammary prostheses, anti-eschar cushions or anti-eschar mattresses, and
- the use characterized in that the aluminosilicate is a zeolite and preferably a synthetic zeolite.

The nonlimiting examples that follow show various possibilities of formulation of the compositions according to the invention and also the characteristics and properties of the silicone gels obtained by crosslinking said compositions.

EXAMPLES

1) The List Below Describes the Starting Materials Used in the Compositions of Parts A and B of this Gel:

Oil (A) (SiVi)=α,ω(dimethylvinylsiloxy) polydimethylsiloxane oil of viscosity 100 000 mPa·s, Oil (B) (SiH)=poly(dimethylsiloxy)(siloxymethylhydrogeno)-α,ω-(dimethylhydrogenosiloxy) oil of viscosity 25 mPa·s, Oil (C) (PDMS)=α,ω(trimethylsiloxy) polydimethyl siloxane of viscosity 100 mPa·s, Slurry (D): mixture of polydimethylsiloxane oil containing vinyl end groups+30% by weight of amorphous fumed silica, Oil (E) (cyclic $D^{VT}$): methylvinylcyclosiloxane, Mixture (F): 10% by weight of an α,ω(trimethylsiloxy) poly(siloxymethylhydrogeno) oil (structure MD'$_{50}$M), in a polydimethylsiloxane oil of viscosity 50 mPa·s, Oil (G) (SiH) α,ω(trimethylsiloxy)poly(dimethylsiloxy)(siloxymethylhydrogeno) oil of viscosity 10 mPa·s, Catalyst (F)=organometallic platinum complex in solution used as crosslinking catalyst; the concentrations of this catalyst are given as weight percentage of Pt metal of oxidation state 0 relative to the total mass of the composition.

2) Table 1 Describes the Concentrations of each of these Constituents in Parts A and B:

TABLE 1

Constitution of the test compositions:

| Constituents | Composition | |
|---|---|---|
| | Part A | Part B |
| | Weight concentration (%) | |
| Oil (C) (PDMS) | 86.62 | 84.82 |
| Oil (A) (SiVi) | 13.19 | 10.48 |
| Catalyst (F) | 0.10 | / |
| Oil (E) (cyclic $D^{I7}$) | 0.09 | 0.54 |
| Oil (B) (SiH) | / | 0.33 |
| Mixture (F) | / | 0.03 |
| Slurry (D) | / | 0.25 |
| Oil (G) (SiH) | / | 3.55 |
| Total | 100 | 100 |

The composition described is in two-component form and the crosslinking takes place after mixing the two parts named A and B in a 50/50 ratio at 25° C. A comparative gel (C-1) is thus obtained.

A second gel (I-1), according to the invention, is prepared by mixing the parts A and B described above (1:1) to which is added 0.05% by weight, relative to the total weight of the composition, of a zeolite Abscents® 1000 sold by the company UOP.

Test to Evaluate the Release of Odor:

Pieces with an area of 2 cm² of a polyurethane film sold by the company Pharetra (film thickness: from 60 to 70 microns) are incorporated into these gels, (C-1) and (I-1), and the whole is then vulcanized at 120° C. for 1 hour 30 minutes. The test results are given in Table 2.

TABLE 2

Tests after vulcanization

| | Presence of nauseating odors (amine-like) |
|---|---|
| Gel C-1 (comparative) | YES |
| Gel (I-1) invention | NO |

The gel according to the invention (I-1) has no nauseating odor (no amine-like odor), whereas the gel according to the comparative example (C-1) has a strong nauseating odor.

The same results (absence of nauseating odor) were obtained using the silicone gel according to the invention as filling material for a closed envelope formed from a polyurethane-based supple material in the manufacture of an external mammary prosthesis, an anti-eschar cushion and an anti-eschar mattress.

The invention claimed is:

1. An external mammary prosthesis, orthopedic cushion, anti-eschar cushion or anti-eschar mattress comprising a closed envelope formed from a polyurethane-based plastic film or a silicone elastomer, said closed envelope comprising a filling material comprising a crosslinked silicone gel that is the hydrosilylation product of at least one polyorganosiloxane (A) containing on average two alkenyl groups bonded to silicon per molecule, said alkenyl groups each containing 2 to 6 carbon atoms, and no silicon atom being bonded to more than one alkenyl group, and at least one hydrogen-bearing silicone compound (B) containing at least two hydrogen atoms bonded to silicon per molecule, and optionally, at least one nonfunctionalized polyorganosiloxane (C), said silicone gel comprising at least one antiodor active principle selected from the group consisting of an aluminosilicate, a cyclodextrin and a compound having an open or closed cage structure, wherein said gel does not exhibit an amine-like odor when compared to a similar gel that does not comprise said antiodor active principle.

2. The external mammary prosthesis, orthopedic cushion, anti-eschar cushion or anti-eschar mattress as claimed in claim 1, wherein the aluminosilicate is a zeolite.

3. The external mammary prosthesis, orthopedic cushion, anti-eschar cushion or anti-eschar mattress as claimed in claim 1, wherein of said antiodor active principle is present at up to 1% by weight, relative to the weight of said hydrogen-bearing silicone compound B.

4. The external mammary prosthesis, orthopedic cushion, anti-eschar cushion or anti-eschar mattress of claim 3, said antiodor principle is present at up to 0.5% by weight, relative to the weight of said hydrogen-bearing silicone compound B.

5. The external mammary prosthesis, orthopedic cushion, anti-eschar cushion or anti-eschar mattress of claim 3, wherein said antiodor principle is present at between 0.01% and 0.1% by weight, relative to the weight of said hydrogen-bearing silicone compound B.

6. The external mammary prosthesis, orthopedic cushion, anti-eschar cushion or anti-eschar mattress of claim 1, wherein said at least one hydrogen-bearing silicone compound (B) contains at least three hydrogen atoms bonded to silicon per molecule.

7. The external mammary prosthesis, orthopedic cushion, anti-eschar cushion or anti-eschar mattress of claim 6, wherein the aluminosilicate is a synthetic zeolite.

8. The external mammary prosthesis, orthopedic cushion, anti-eschar cushion or anti-eschar mattress as claimed in claim 6, wherein said antiodor active principle is present at up to 1% by weight, relative to the weight of said hydrogen-bearing silicone compound B.

9. The external mammary prosthesis, orthopedic cushion, anti eschar cushion or anti-eschar mattress as claimed in claim 8, wherein said antiodor active principle is present at up to 0.5% by weight, relative to the weight of said hydrogen-bearing silicone compound B.

10. The external mammary prosthesis, orthopedic cushion, anti-eschar cushion or anti-eschar mattress as claimed in claim 8, wherein said antiodor active principle is present at between 0.01% and 0.1% by weight, relative to the weight of said hydrogen-bearing silicone compound B.

* * * * *